United States Patent [19]

Anderson

[11] 4,275,032
[45] Jun. 23, 1981

[54] ALKYLATION COMBINED SETTLER-SOAKER APPARATUS

[75] Inventor: Robert F. Anderson, La Grange, Ill.

[73] Assignee: UOP Inc., Des Plaines, Ill.

[21] Appl. No.: 56,763

[22] Filed: Jul. 12, 1979

[51] Int. Cl.² ............................................. G01N 29/02
[52] U.S. Cl. ..................................... 422/110; 422/189; 422/111; 422/224; 422/256; 422/234; 585/719; 585/723; 210/521
[58] Field of Search ................. 422/62, 110, 111, 115, 422/230, 234, 236, 256, 258, 224, 226, 228, 189; 210/522, 536, 537, 538, 521; 585/719, 723

[56] References Cited

U.S. PATENT DOCUMENTS

| | | | |
|---|---|---|---|
| 1,750,922 | 3/1930 | Cheakas et al. | 210/537 |
| 2,729,550 | 1/1956 | Maycock et al. | 422/256 |
| 2,939,771 | 6/1960 | McDonald et al. | 422/256 |
| 3,247,104 | 4/1966 | Sako et al. | 422/256 |
| 3,825,616 | 7/1974 | Chapman | 585/719 |
| 3,901,536 | 3/1975 | Borst, Jr. | 585/723 |
| 4,019,869 | 4/1977 | Morris | 422/256 |
| 4,134,734 | 1/1979 | Winter | 422/224 |
| 4,167,535 | 9/1979 | Carson | 585/719 |

FOREIGN PATENT DOCUMENTS

| | | | |
|---|---|---|---|
| 640252 | 4/1962 | Canada | 585/719 |
| 745203 | 10/1966 | Canada | 585/723 |

Primary Examiner—S. Leon Bashore
Assistant Examiner—Chris Konkol
Attorney, Agent, or Firm—James R. Hoatson, Jr.; Robert W. Welch; William H. Page, II

[57] ABSTRACT

A settler-soaking apparatus for treating the effluent from an acid-catalyzed alkylation reaction is disclosed which comprises three interconnected vertically aligned chambers. The uppermost chamber possesses a hydrocarbon outlet means above an acid hydrocarbon inlet means and a downspout having an acid transfer means extending through and ending in the lower end of the middlemost chamber. The latter possesses a hydrocarbon outlet means at an elevated position with respect to the end of the acid transfer means in the downspout and a lower situated acid outlet means. The lowermost chamber possesses a multitude of spaced horizontal perforate trays and an acid hydrocarbon inlet means, which is in connection with the hydrocarbon outlet means of the uppermost chamber. The middle and lowermost chamber are in open communication via a chimney which extends upwardly into said middle chamber to provide a hydrocarbon outlet means at a point above the end of said downspout.

3 Claims, 1 Drawing Figure

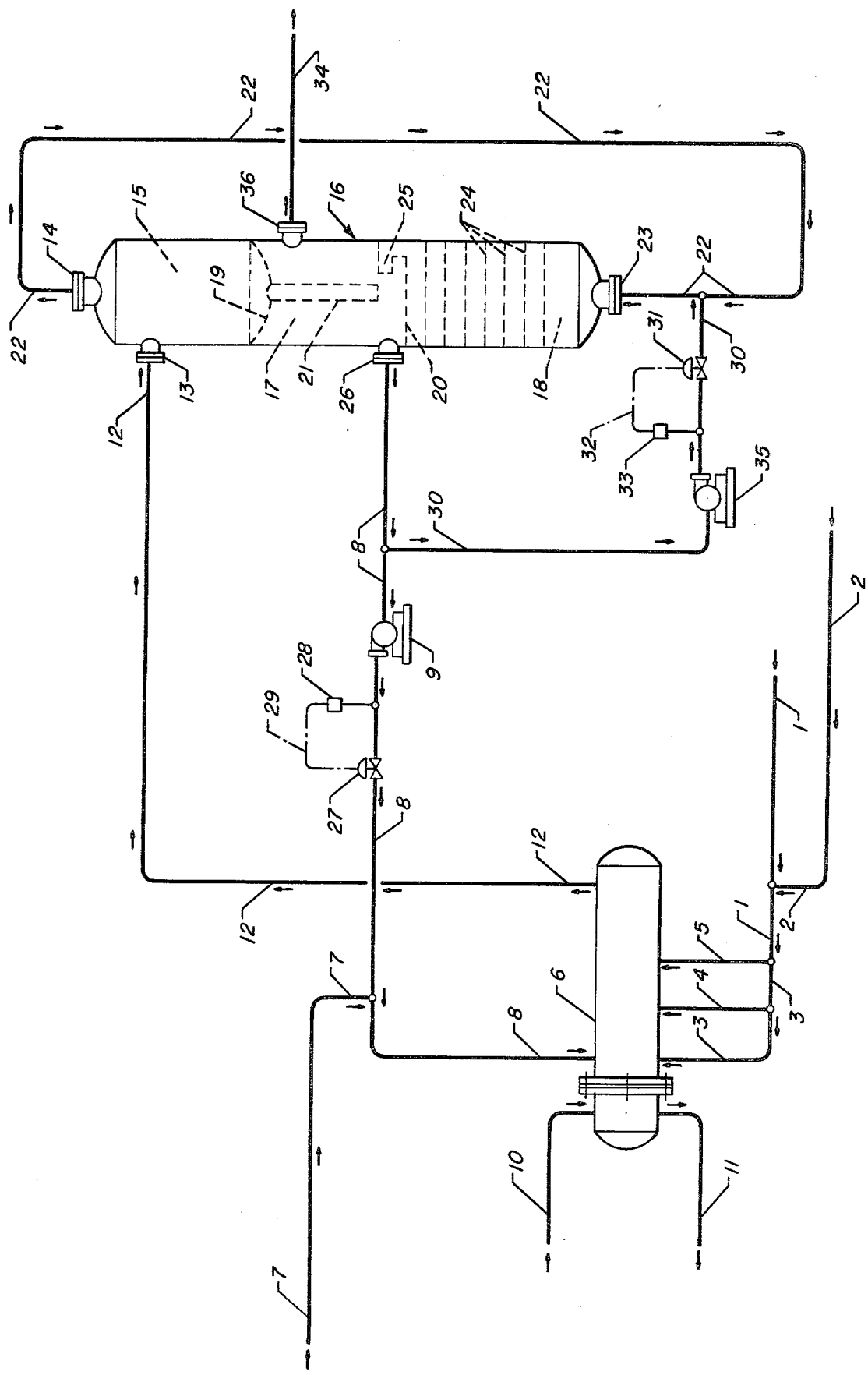

ALKYLATION COMBINED SETTLER-SOAKER APPARATUS

This invention relates to the acid-catalyzed alkylation of an alkylatable hydrocarbon with an olefin-acting alkylating agent. More specifically, this invention relates to the hydrofluoric acid-catalyzed alkylation of an isoparaffin with an olefin alkylating agent. The hydrofluoric acid-catalyzed alkylation of an isoparaffin such as isobutane and isopentane, with an olefin such as propylene, butylene and amylene, or an olefin-acting compound such as the $C_3$–$C_5$ alkyl halides, is a well known and commercially important process for the production of gasoline boiling range hydrocarbons collectively referred to as alkylate. This alkylate is characterized by a high motor and research octane rating making it a highly desirable blending agent for the upgrading of gasoline stocks otherwise incapable of meeting the octane requirements of modern automobile engines. This high octane alkylate assumes even greater importance as a gasoline blending agent with the continuing phase-out of lead alkyl compounds as an octane promoter, and it is a continuing goal to provide an economically attractive process which yields an alkylate product of improved octane characteristics.

Conventional hydrofluoric acid-catalyzed alkylation schemes generally employ isobutane as the isoparaffin, and propylene, butylenes and amylenes, or mixtures thereof, as the olefin-acting alkylating agent. The isoparaffin, olefin-acting alkylating agent and the acid catalyst are thoroughly admixed in an alkylation reactor, and the reaction mixture is processed through the reactor as an emulsion. The alkylation reaction is substantially complete in a relatively short time, and the reaction mixture is withdrawn from the reactor and allowed to settle into immiscible hydrocarbon and acid phases. The lower acid phase thus separated is recycled to the alkylation reactor for further catalytic use, and the upper hydrocarbon phase is further processed, e.g., by fractionation, to recover the alkylate product, and to separate unreacted isoparaffin for recycle and further use in the alkylation reactor.

In order to achieved an acceptable yield of high quality alkylate, it has been found necessary to effect the alkylation reaction at fairly specific reaction conditions. For example, it has been found necessary to maintain a relatively high catalyst/hydrocarbon volume ratio in the alkylation reactor to obviate any undue polymerization of the olefin alkylating agent which would otherwise occur. It is well known to the art that olefin polymerization is an undesirable side reaction consuming large amounts of the olefin reactant and adversely affecting product yield and producing relatively high boiling hydrocarbon polymers of low octane value. Thus, it has been found essential to the production of an acceptable yield of high quality alkylate that the catalyst/hydrocarbon volume ratio be maintained at a relatively high level in the alkylation reactor, generally in the range of from about 1:1 to about 2:1.

The conventional alkylation scheme has heretofore been modified to include a reaction mixture soaker, a relatively large-vessel equipped with mixing means such as perforated trays, baffle sections, and the like, for maintaining the reaction mixture as an emulsion. The hydrocarbon reactants and the acid catalyst are initially contacted and thoroughly admixed in the alkylation reactor which is equipped with heat exchange means. Within a relatively brief period, substantially all of the olefin-acting alkylating agent is reacted with the isoparaffin, and the resulting exothermic heat of reaction is taken up by said heat exchange means to maintain a predetermined, substantially uniform, alkylation reaction temperature. After a relatively brief contact period, generally less than about two minutes, the reaction mixture is passed from the reactor to the aforementioned reaction mixture soaker which does not contain heat exchange means. The reaction mixture is maintained in contact in said soaker for a more extended period of up to about 60 minutes, and thereafter removed to a conventional settler wherein the hydrocarbon-immiscible acid is allowed to settle with the formation of an upper hydrocarbon phase and a lower acid phase therein. The inclusion of a reaction mixture soaker in the alkylation scheme has been found to effect a substantial improvement in the motor and research octane ratings of the alkylate product. This is believed to be due to the isomerization of relatively low octane alkylate components, such as dimethylhexanes, to form additional quantities of relatively high octane alkylate components, such as trimethylpentanes. Use of the reaction mixture soaker has also resulted in a reduced concentration of undesirable alkyl halides in the alkylate product.

Although use of the reaction mixture soaker provides an overall improvement in the alkylation operation, the relatively long reaction mixture retention time in the soaker necessitates an unduly large inventory of the acid alkylation catalyst, a major portion of which is contained in the soaker at any given time. The larger catalyst inventory entails the use of larger equipment in several areas of the alkylation operation, the increased cost of which partially offsets the advantages derived through use of the reaction mixture soaker. For example, every alkylation operation will typically include a catalyst storage drum of sufficient size to contain, when necessary, the total inventory of catalyst employed in the alkylation operation. The drum is used for catalyst storage during shut-down periods in the alkylation operation. When the catalyst inventory is increased to accommodate a reaction mixture soaker, the size of the drum must be increased accordingly. In any case, the advantages derived through use of a reaction mixture soaker have been, to some extent, hindered by the large catalyst inventory required, and by the increased investment and operating costs associated therewith.

It is therefore an object of this invention to provide an improved process for the acid-catalyzed alkylation of an alkylatable hydrocarbon with an olefin-acting alkylating agent.

It is a more specific object to provide an improved process for the hydrofluoric acid-catalyzed alkylation of an isoparaffin with an olefin alkylating agent affording the benefits of an alkylation reaction mixture soaker and a substantial reduction in the acid catalyst inventory required therein.

Another object of this invention comprises providing an apparatus for the treatment of the reactor effluent from an acid-catalyzed alkylator. In essence, this apparatus is a settler-soaking apparatus having three vertically aligned chambers. The uppermost chamber has a hydrocarbon outlet means above an acid-hydrocarbon inlet means and a downspout having an acid transfer means extending into the middle chamber and terminating in the lower end of the middle chamber. This middle chamber has a hydrocarbon outlet means at an elevated position with respect to the discharge end of the acid transfer means of the connecting downspout and a lower situated acid outlet means. The lowermost chamber possesses a multitude of spaced horizontal perforate trays and an acid-hydrocarbon inlet means in connection with the hydrocarbon outlet means of the uppermost chamber. The middle and lowermost chamber are in open communication via a chimney which extends upwardly into the middle chamber to provide a hydrocarbon outlet means at a point above the end of said downspout.

Thus, in one of its broad aspects, the present invention embodies the improvement which comprises charging said alkylation reaction mixture to an upper settling chamber of a unitary soaker-settler vessel comprising said upper settling chamber, a middle settling chamber and a lower soaking chamber, and forming an upper hydrocarbon phase and a lower hydrocarbon-immiscible acid phase therein; transferring said hydrocarbon phase from said upper chamber to said lower chamber; recovering said acid phase from said upper chamber through a downspout providing passage through an upper hydrocarbon phase contained in said middle chamber, and discharging said acid phase into a lower acid phase contained therein; transferring a portion of the acid phase contained in said middle chamber to said lower chamber, and recycling a remaining portion thereof to said alkylation reactor; admixing the hydrocarbon and acid phases transferred to said lower chamber, processing the mixture upwardly through said chamber, discharging said mixture overhead into said middle chamber, and separating said mixture therein to provide the aforementioned upper hydrocarbon phase and a portion of the aforementioned lower acid phase contained therein; and withdrawing said hydrocarbon phase from said middle chamber and separating the alkylate product therefrom.

One of the more specific embodiments concerns an improvement in the hydrofluoric acid-catalyzed alkylation of isobutane with a propylene-butylene mixture and comprises charging the alkylation reaction mixture to an upper settling chamber of a unitary soaker-settler vessel comprising said upper settling chamber, a middle settling chamber and a lower soaking chamber, and forming an upper hydrocarbon phase and a lower hydrocarbon-immiscible acid phase therein; transferring from about 90 to about 100 volume percent of said hydrocarbon phase from said upper chamber to said lower chamber; recovering from about 90 to about 100 volume percent of said acid phase from said upper chamber through a downspout providing passage through an upper hydrocarbon phase contained in said middle chamber and discharging said acid phase into a lower acid phase contained therein; transferring from about 5 to about 10 volume percent of the acid phase contained in said middle chamber to said lower chamber, and recycling the remaining portion thereof to said alkylation reactor; admixing the hydrocarbon and acid phases transferred to said lower chamber, processing the mixture upwardly through said chamber to provide an average residence time therein of from about 1 to about 60 minutes, discharging said mixture overhead into said middle chamber, and separating said mixture therein to provide the aforementioned upper hydrocarbon phase and a portion of the aforementioned lower acid phase contained therein; and withdrawing said hydrocarbon phase from said middle chamber and separating the alkylate product therefrom.

This invention further embodies a combination soaker-settler apparatus for treating a reaction mixture from an acid-catalyzed alkylation reaction which comprises an elongated, vertically-aligned, cylindrical vessel having an upper settling chamber, a middle settling chamber and a lower soaking chamber, said vessel being separated into said chambers by means of an upper imperforate plate and a lower imperforate plate traversing said vessel in a horizontal plane, and said chambers having outer walls in common with said vessel; said upper chamber having an acid-hydrocarbon inlet means at a level below a hydrocarbon outlet means, and said chamber being in open communication with said middle chamber through a downspout having an acid inlet in a bottom portion of said upper chamber, and extending downwardly through said upper imperforate plate to provide an outlet at a point in the lower portion of said middle chamber; said middle chamber having an acid outlet means in a lower portion thereof and a hydrocarbon outlet means in the upper portion thereof; said lower chamber comprising a multitude of spaced, perforate trays traversing said chamber in a horizontal plane, said chamber further comprising an acid-hydrocarbon inlet means in the lower portion thereof, and said chamber being in open communication with said middle chamber through a chimney in said lower imperforate plate extending upwardly into said middle chamber to provide a hydrocarbon outlet at a point above the outlet of said downspout; said hydrocarbon outlet means in said upper chamber discharging into an external hydrocarbon transfer conduit which passed downwardly and discharges into said acid hydrocarbon inlet means in said lower chamber.

Other objects and embodiments of this invention will become apparent in the following detailed specification.

The further description of the invention is presented with reference to the attached drawing which is a schematic representation of one preferred embodiment of the invention. With reference to the drawing, an isoparaffin reactant stream typically comprising from about 60 to about 95 mole percent isobutane, is charged to the alkylation process by way of line 1. The olefin-acting alkylating agent, typically a mixture of propylene and butylenes, is admitted to the process by way of line 2 and admixed with the isoparaffin reactant passing through line 1 to provide a hydrocarbon reactant stream having an isoparaffin/olefin-acting alkylating agent mole ratio of from about 4:1 to about 30:1, and preferably from about 8:1 to about 15:1. The hydrocarbon reactant stream is continued through line 1 and dispersed through multiple lines 3, 4 and 5 to an alkylation reactor 6. In this manner, a more efficient mixing of the hydrocarbon reactants and the acid catalyst is effected, and an excessive generation of heat in any one section of the alkylation reactor is substantially obviated. Make-up acid alkylation catalyst, for example, substantially anhydrous hydrofluoric acid, is admitted to the alkylation process through line 7, and said acid is charged to the alkylation reactor 6 in admixture with acid catalyst recycled to said reactor through line 8 by means of an acid recycle pump 9. Although not shown, the alkylation reactor 6 will advantageously comprise a predetermined number of baffle means, for example standard exchange type baffles, to provide a pressure drop of from about 5 to about 25 psi. and promote the formation of a homogeneous reaction mixture throughout the alkylation reactor. While the alkylation reactor depicted in the drawing serves to illustrate the process of this invention, it is understood that other reactors known to the art may suitably be employed.

Substantially all of the olefin-acting alkylating agent is consumed in the alkylation reaction over a relatively brief period, and said reaction is accompanied by a considerable evolution of heat. Accordingly, cooling water is charged to the alkylation reactor 6 through line 10 and circulated in indirect heat exchange relationship with the hot reaction mixture using conventional heat exchange means not shown. Spent cooling water is discharged via line 11.

Alkylation reaction conditions maintained in the alkylation reactor 6 include a temperature of from about 0° to about 200° F., preferably from about 30° to about 110° F., and a pressure of from about atmospheric to about 500 psi. and sufficient to maintain substantially liquid phase reaction conditions. Generally, the pressure will be in the 200–300 psi. range. The reaction mixture is processed through the alkylation reactor 6 at a rate to allow an average residence time therein of from about 1 to about 5 minutes, and generally less than about 2 minutes. The hydrocarbon reactant stream and the acid alkylation catalyst are charged to the alkylation reactor 6 at relative rates sufficient to provide an acid/hydrocarbon volume ratio of from about 1:1 to about 2:1. The alkylation reactor effluent is recovered through line 12 as an emulsion substantially free of the olefin-acting alkylating agent and comprising unreacted isoparaffin, alkylate, and the hydrocarbon-immiscible acid alkylation catalyst.

The acid-hydrocarbon mixture is transferred by way of line 12 to an acid-hydrocarbon inlet means 13 located at a level below a hydrocarbon outlet means 14 in an upper settling chamber 15 of a unitary, elongated, vertically aligned, cylindrical settling-soaking vessel 16. The settling-soaking vessel 16 is separated into said upper chamber 15, a middle settling chamber 17 and a lower soaking chamber 18 by means of an upper imperforate plate 19 and a lower imperforate plate 20 traversing said vessel in a horizontal plane. Separation of the hydrocarbon and acid phases in said upper settling chamber 15 is not necessarily completed therein. Preferably, from about 92 to about 100 volume percent of the acid is recovered in the lower acid phase and, correspondingly, from about 92 to about 100 volume percent of the hydrocarbon is recovered in the upper hydrocarbon phase. In any case, the acid phase is allowed to gravitate downwardly from said upper settling chamber 15 through a downspout 21 having an acid inlet in a bottom portion of said upper settling chamber 15 and extending downwardly through said upper imperforate plate 19 to provide an outlet in the lower portion of said middle settling chamber 17, said gravitating acid phase being discharged into a lower portion of said middle settling chamber 17. The upper hydrocarbon phase which accumulates in the upper settling chamber 15, preferably comprising less than about 10 volume percent acid, is withdrawn through the hydrocarbon outlet means 14 and transferred by way of an external hydrocarbon transfer conduit 22 directly to an acid-hydrocarbon inlet means 23 in the lower portion of said soaking chamber 18.

The hydrocarbon phase transferred through the external hydrocarbon transfer conduit 22 is charged to said lower soaking chamber 18 in admixture with an acid phase recovered from the aforementioned middle settling chamber 17 as hereinafter related. The purpose of the soaking chamber is to build as much time as needed into the alkylation reaction so that a complete alkylation reaction can occur. Thus, the acid-hydrocarbon mixture, with an acid-hydrocarbon volume ratio of from about 0.05:1 to about 0.3:1, is processed upwardly through said soaking chamber 18 at a rate to provide an average residence time therein of from about 1 to 60 minutes. In the drawing, the lower soaking chamber 18 comprises a multitude of spaced perforate plates, decks or trays 24 traversing said chamber in a horizontal plane. The lower soaking chamber is designed to provide a pressure drop of from about 5 to about 25 psi. to promote a homogeneous reaction mixture therein. Soaking conditions include a temperature of from about 0° to about 200° F., and preferably from about 30° to about 110° F. Sufficient pressure is employed to maintain substantially liquid phase soaking conditions. In any case, the acid-hydrocarbon mixture is recovered from the lower soaking chamber 18 through an overhead chimney 25 in said lower imperforate plate 20 and extending upwardly into said middle settling chamber 17 to provide an outlet at a point above the outlet of said downspout 21. The acid-hydrocarbon mixture is discharged into the aforementioned middle settling chamber 17 wherein the mixture is allowed to settle and effect a substantially complete separation of the acid and hydrocarbon components. The acid-hydrocarbon mixture discharged from the lower soaking chamber 18 into the middle settling chamber 17 will thus provide an upper hydrocarbon phase in said middle settling chamber and a portion of the aforementioned lower acid phase contained therein. The upper hydrocarbon phase is withdrawn from said middle settling chamber 17, and from said unitary vessel 16, by way of a hydrocarbon outlet means 36 in the upper portion of said chamber and recovered substantially acid-free through line 34. Said hydrocarbon phase is further processed for the recovery of alkylate, and for the recovery and recycle of unreacted isoparaffin, by conventional means, not shown.

The lower acid phase is recovered from said middle settling chamber 17 through an acid outlet means 26 in a lower portion thereof. The acid phase is recovered substantially free of said hydrocarbon phase and passes through an external acid transfer conduit 8 to a circulating pump 9. While the bulk of the acid phase is continued through acid transfer conduit 8 for recycle to the alkylation reactor 6, one portion comprising from about 5 to about 25 volume percent of the total is diverted through an acid recycle conduit 30 and a circulating pump 35 to be admixed with the aforementioned hydrocarbon phase transferred to the lower soaking chamber 18 through line 22. Acid recycle conduit 30 includes a flow control valve 31 interconnected through a signal transfer means 32 to a flow detection and signal generation means 33 located upstream of said flow control valve. As heretofore stated, the bulk of the acid phase recovered from said middle settling chamber 17 is continued through the external acid transfer conduit 8 for recycle to the alkylation reactor 6. The acid is recycled by means of a circulating pump 9 through a flow control valve 27, said flow control valve being interconnected through a signal transfer means 29 to a flow detection and signal generation means 28 located upstream of said flow control valve.

The practice of the present invention provides the benefits attendant a relatively high acid/hydrocarbon volume ratio in the alkylation reactor, and substantially obviates the unduly large acid inventories heretofore associated with a reaction mixture soaker while retaining the benefits thereof. Since a major portion of the total acid inventory in use in the alkylation process is processed only through the upper and middle settling chambers and recycled to the alkylation reactor to provide a desirable relatively high catalyst/hydrocarbon volume ratio therein, and since only a minor portion of said total acid inventory, sufficient to promote the octane improving effect of a reaction mixture soaker, is tied up in the lower soaking chamber at any given time, a very significant reduction in the overall acid inventory is achieved.

The alkylation process of the present invention is of particular advantage with respect to the alkylation of $C_4$–$C_6$ isoparaffinic hydrocarbons, particularly isobutane, isopentane, and mixtures thereof, and especially isobutane. A suitable isoparaffin feedstock may contain normal paraffins or other nonreactive contaminants of a similar nature. For example, commercially available isobutane feedstocks will typically comprise from about 60 to about 95 wt.% isobutane, from about 4 to about 35 wt.% n-butane and from about 1 to about 5 wt.% propane. Suitable olefin-acting alkylating agents include the $C_3$–$C_6$ olefins, alkyl halides, and mixtures thereof. The $C_3$–$C_6$ olefins are preferred. Many available olefinic feedstocks comprise a mixture of propylene, butylenes and/or amylenes, and such mixtures are suitably employed. Similarly, a mixture of $C_3$–$C_5$ alkyl halides and olefinic hydrocarbons is also suitable. The preferred $C_3$–$C_5$ olefinic hydrocarbons are frequently in a feedstock derived as a product or by-product of one or more petroleum refining processes, said feedstock further containing lighter and heavier olefins as well as paraffins, and said feedstocks are commonly employed and suitable for use in the process of this invention.

The acid alkylation catalyst utilized in the process of this invention is preferably hydrofluoric acid. Generally, the acid catalyst will comprise from about 75 to about 95 wt.% of titratable hydrofluoric acid, less than about 5 wt.% water, and a balance consisting of organic diluent materials. A particularly preferred acid alkylation catalyst comprises from about 80 to about 90 wt.% hydrofluoric acid and less than about 1 wt.% water.

There are a number of alkylation reactors known to the art which can be utilized in the present alkylation process. For example, the alkylation reactor described in U.S. Pat. Nos. 3,133,128; 3,456,033; 3,469,949; 3,501,536; 3,787,518; 3,780,131; etc., are suitably employed in the present process.

Alkylation reaction conditions employed in the alkylation reactor include a temperature of from about 0° to about 200° F. and a pressure in the range of from about atmospheric to about 500 psi. and sufficient to maintain substantially liquid phase reaction conditions. The acid catalyst is employed with the hydrocarbon reactants in a volume ratio of from about 1:1 to about 2:1, or more, and the isoparaffin and olefin-acting alkylating agent are employed in a mole ratio of from about 4:1 to about 30:1, and preferably from about 8:1 to about 15:1. Alkylation reaction conditions further include a contact time in the alkylation reactor of from about 0.1 to about 5 minutes. When the preferred reactants, isobutane and $C_3$–$C_5$ olefins, are employed, preferred alkylation reaction conditions include a temperature of from about 30° to about 110° F., a contact time in said reactor of from about 0.2 to about 2 minutes, and a pressure of from about 200 to about 300 psi.

In order to illustrate one of the more specific embodiments of this invention, a system identical to that illustrated in the attached drawing is employed. Isobutane is charged to the alkylation processes by way of line 1 at the rate of about 720 barrels per hour. Mixed propylene and butylenes are admitted to the process by way of line 2 at the rate of about 60 barrels per hour, and said olefins are admixed with the isobutane reactant passing through line 1. The hydrocarbon reactant stream is continued through line 1 and dispersed through multiple lines 3, 4 and 5 to an alkylation reactor 6. Substantially anhydrous hydrofluoric acid is charged to the alkylation reactor from line 8 at the rate of 1170 barrels per hour as hereinafter shown. Alkylation conditions maintained in the alkylation reactor 6 include a temperature of from about 30° to about 110° F., and a pressure of from about 200 to about 300 psi. The reaction mixture is processed through the alkylation reactor 6 at a rate to allow an average residence time therein of from about 0.2 to about 2 minutes. The alkylation reactor effluent is recovered through line 12, and transferred by way of line 12 to an upper settling chamber 15 of an elongated, unitary vessel 16. In the upper settling chamber 15, the acid is allowed to settle and gravitate downwardly to form a lower acid phase and an upper hydrocarbon phase therein. The acid phase is allowed to gravitate downwardly from said upper settling chamber 15 through a conduit 21 at the rate of 1170 barrels per hour to be discharged into a lower portion of a middle settling chamber 17. The upper hydrocarbon phase which accumulates in the upper settling chamber 15 is withdrawn through line 22 at the rate of about 752 barrels per hour and transferred directly to a lower soaking chamber 18. The hydrocarbon phase is charged to said lower soaking chamber in admixture with hydrofluoric acid recovered from the aforementioned middle settling chamber 17 and passing through an acid recycle conduit 30 at the rate of 75.2 barrels per hour as hereinafter related. The acid-hydrocarbon mixture is processed upwardly through said lower soaking chamber 18 at a rate to provide an average residence time therein of about 10 minutes. Soaking conditions further include a temperature of from about 30° to about 110° F. and a pressure of from about 200 to about 300 psi. The lower soaking chamber 18 is designed to provide a pressure drop of from about 5 to about 25 psi. The acid-hydrocarbon mixture is recovered from a lower soaking chamber 18 through an overhead chimney 25 and discharged into the middle settling chamber 17 wherein the mixture is allowed to settle and effect a substantially complete separation of the acid and hydrocarbon components. The acid-hydrocarbon mixture discharged from the lower soaking chamber 18 into the middle settling chamber 17 will thus provide an upper hydrocarbon layer in said middle settling chamber 17 and a portion of the lower acid phase contained therein. The upper hydrocarbon phase is withdrawn from said middle settling chamber 17, and from said unitary soaking-settling vessel 16, by way of line 34 at the rate of 752 barrels per hour. Said hydrocarbon phase is further processed for the recovery of alkylate product, and for the recovery and recycle of unreacted isobutane, by conventional means, not shown.

The lower acid phase is recovered from the middle settling chamber 17 through an external acid transfer conduit 8 at a rate of about 1245.2 barrels per hour. About 75.2 barrels of acid per hour are diverted from said acid transfer conduit 8 through an acid recycle conduit 30 and passed through a circulating pump 35 to be admixed with the aforementioned hydrocarbon phase transferred to the lower soaking chamber 18 by way of the external hydrocarbon transfer conduit 22. The acid recycle conduit 30 includes a flow control valve 31 interconnected through a signal transfer means 32 to a flow detection and signal generation means 33 located upstream of said control valve. The balance of the lower acid phase from said middle settling chamber 17, about 1170 barrels per hour, is continued through the external acid transfer conduit 8 for recycle to the alkylation reactor 6. The acid is recycled by means of a circulating pump 9 through a flow control valve 27, said flow control valve being interconnected through a signal transfer means 29 to a flow detection and signal generation means 28 located upstream of said flow control valve.

I claim as my invention:

1. A combination soaking-settling apparatus for treating a reaction mixture from an acid-catalyzed alkylation reaction which comprises an elongated, vertically aligned, cylindrical vessel having an upper settling chamber, a middle settling chamber and a lower soaking chamber, said vessel being separated into said chambers by means of an upper imperforate plate and a lower imperforate plate traversing said vessel in a horizontal plane, and said chambers having outer walls in common with said vessel;

said upper chamber having an acid-hydrocarbon inlet means at a level below a hydrocarbon outlet means, and said chamber being in open communication with said middle chamber through a downspout having an acid inlet in a bottom portion of said upper chamber, and extending downwardly through said upper imperforate plate to provide an outlet at a point in the lower portion of said middle chamber;

said middle chamber having an acid outlet means in a lower portion thereof and a hydrocarbon outlet means in the upper portion thereof;

said lower chamber comprising a multitude of spaced, perforate trays traversing said chamber in a horizontal plane, said chamber further comprising an acid-hydrocarbon inlet means in the lower portion thereof, and said chamber being in open communication with said middle chamber through a chimney in said lower imperforate plate extending upwardly into said middle chamber to provide a hydrocarbon outlet at a point above the outlet of said downspout;

said hydrocarbon outlet means in said upper chamber discharging into an external hydrocarbon transfer conduit which passes downwardly and discharges into said acid-hydrocarbon inlet means in said lower chamber.

2. The apparatus of claim 1 further characterized in that said acid outlet means of said middle chamber discharges into an external acid transfer conduit having a flow control valve interconnected through a signal transfer means to an acid flow detection and signal means communicating with the internal volume of said conduit at a point upstream of said valve.

3. The apparatus of claim 2 further characterized in that said external acid transfer conduit discharges into an acid recycle conduit at an intermediate point upstream of said acid flow detection and signal means, said acid recycle conduit passing downwardly and discharging into said acid-hydrocarbon inlet means in said lower chamber, said acid recycle conduit having a flow control valve interconnected through a signal transfer means to an acid flow detection and signal means communicating with the internal volume of said conduit at a point upstream of said valve.

* * * * *